US011543380B2

(12) United States Patent
Mohanty et al.

(10) Patent No.: US 11,543,380 B2
(45) Date of Patent: Jan. 3, 2023

(54) SEMICONDUCTOR-SENSOR BASED NEAR-PATIENT DIAGNOSTIC SYSTEM AND METHODS

(71) Applicant: FemtoDx, Inc., Beverly Hills, CA (US)

(72) Inventors: Pritiraj Mohanty, Beverly Hills, CA (US); Shyamsunder Erramilli, Quincy, MA (US)

(73) Assignee: FemtoDx, Inc., Beverly Hills, CA (US)

( * ) Notice: Subject to any disclaimer, the term of this patent is extended or adjusted under 35 U.S.C. 154(b) by 260 days.

(21) Appl. No.: 16/683,456

(22) Filed: Nov. 14, 2019

(65) Prior Publication Data

US 2020/0080963 A1 Mar. 12, 2020

Related U.S. Application Data

(63) Continuation of application No. 15/691,567, filed on Aug. 30, 2017, now abandoned.

(60) Provisional application No. 62/381,137, filed on Aug. 30, 2016.

(51) Int. Cl.
| | |
|---|---|
| *G01R 27/08* | (2006.01) |
| *G01N 27/414* | (2006.01) |
| *G01N 33/487* | (2006.01) |
| *B01L 3/00* | (2006.01) |
| *H04L 67/12* | (2022.01) |

(52) U.S. Cl.
CPC .... *G01N 27/4145* (2013.01); *B01L 3/502715* (2013.01); *B01L 3/502753* (2013.01); *B01L 3/502761* (2013.01); *G01N 33/48792* (2013.01); *B01L 2200/10* (2013.01); *B01L 2300/023* (2013.01); *B01L 2300/0627* (2013.01); *B01L 2300/0645* (2013.01); *B01L 2300/0681* (2013.01); *B01L 2300/0819* (2013.01); *B01L 2300/0877* (2013.01); *B01L 2300/0896* (2013.01); *B01L 2300/12* (2013.01); *B01L 2400/0478* (2013.01); *H04L 67/12* (2013.01)

(58) Field of Classification Search
CPC ............ G01N 27/4143; G01N 27/414; G01N 27/4145; G01N 27/4146; G01N 27/4148; G01N 27/4167; G01N 27/60; G01N 27/62; G01N 27/227; G01N 33/48792; G01N 33/5438; G01N 33/552; G01N 33/227

See application file for complete search history.

(56) References Cited

U.S. PATENT DOCUMENTS

| 7,955,559 B2* | 6/2011 | Joshi | G01N 27/3272 977/723 |
|---|---|---|---|
| 2006/0204428 A1* | 9/2006 | Noy | G01N 27/4146 423/445 R |
| 2007/0264623 A1* | 11/2007 | Wang | B82Y 15/00 422/68.1 |
| 2016/0290957 A1* | 10/2016 | Ram | C12Q 1/6825 |
| 2017/0014822 A1* | 1/2017 | Ker | G01N 27/3272 |
| 2017/0023519 A1* | 1/2017 | Rowe | A61B 5/01 |
| 2018/0038824 A1* | 2/2018 | Shachar | G01N 33/5438 |
| 2018/0313786 A1* | 11/2018 | Rearick | G01N 27/4165 |
| 2019/0317081 A1* | 10/2019 | Taslim | G01N 33/54366 |

* cited by examiner

*Primary Examiner* — Thang X Le
(74) *Attorney, Agent, or Firm* — Wolf, Greenfield & Sacks, P.C.

(57) ABSTRACT

A semiconductor sensor-based near-patient diagnostic system and related methods.

7 Claims, 3 Drawing Sheets

SEMICONDUCTOR-SENSOR BASED NEAR-PATIENT DIAGNOSTIC SYSTEM AND METHODS

RELATED APPLICATIONS

This application is a continuation of U.S. application Ser. No. 15/691,567, filed Aug. 30, 2017, which claims priority to U.S. Provisional Application No. 62/381,137, filed Aug. 30, 2016, which are incorporated herein by reference in their entirety.

BACKGROUND

Recent advances in genomics and proteomics now enable use of biomarkers to detect diseases at an early stage, predict optimal therapy tailor-made for specific patients and monitor therapy responsiveness. Despite the promise of biomarkers in screening, diagnosis and treatment, very few biomarker-based tests are currently in clinical use. There is a lag in the translation of biomarker research into clinically relevant tests, in spite of the potential impact of biomarker testing on cost effectiveness of detection and treatment, and on overall economic burden of care. Though this problem arises due to technical, financial and regulatory challenges linked to the development and incorporation of biomarker testing into clinical practice, the central problem seems to be the lack of a low-cost platform technology that can be employed at the point of care within the current clinical workflow.

Specifically in cancer care, there is a need for developing tools that can rapidly classify the individual patient's disease according to its molecular "fingerprint", which may include detecting the presence of hundreds of biomarkers or genes. Such a tool must generally also be relatively inexpensive, in particular for more frequent testing and monitoring at the point of care or in a near-patient setting.

There is a need for near-patient testing for markers for heart attack and stroke that can be employed at the point of care (e.g., home, ambulance, doctor's office, etc). Such a test must generally be done with a device that is small and portable, inexpensive and easy to use. In addition to the need for use by untrained professionals, it is also generally important for the device to provide the test results in a short time frame (for instance, seconds to minutes) so that immediate treatment can be performed. Fast diagnosis is in particular important for disease-related events such as heart attack or stroke that are time critical. In addition, it is generally important for the test results to be shared among care provider professionals including doctors, nurses, emergency service providers and specialists. Furthermore, analysis of the test results may be performed in situ (within the device) or remotely (using cloud-based computing). Such analytics may aid the clinician in providing the best actionable decision. Therefore, it can also be important for the device to possess connectivity (via wifi, Bluetooth or other forms of wireless or wired communication systems) to perform a two-way communication (send and receive) for data analytics and decision-making process.

The current standard in diagnosis and monitoring using biomarkers is a central-lab based device that is expensive and cannot be used at the point of care. This application describes a working prototype, which is a handheld device that enables low-cost testing of the exact same analyte at the same clinically relevant level. This device is based on nanosensor technology, using which a wide variety of biomarkers have been detected at the required clinical levels for early diagnosis, staging and monitoring of therapy.

Furthermore, it has been possible to miniaturize the prototype into a smartphone plugin, where the plugin or the cartridge contains the sensor, microfluidics and measurement electronics, and the smartphone acts as a reader. The disposable plugin cartridge is designed to work with a smartphone to perform multiplexed tests of multiple analytes. In addition to the hardware necessary for detection of multiple markers at the required levels of sensitivity and specificity, the output data is designed to comply with necessary analytics (through multivariate regression analysis and other probabilistic distribution methods) for the proper interpretation and actionable decision by the necessary users and stakeholders (patient, doctor, caregiver, payer etc).

SUMMARY

A semiconductor sensor-based near-patient diagnostic system and related methods are described herein.

In one aspect, a device is provided. The device comprises a sensor module including a sensor chip configured to sense chemical or biological entities and a reader module configured to send control and command signals to the sensor module to perform a task. The device further comprises a communication channel configured so that the reader module and the sensor module have a two-way communication.

In another aspect, a device is provided. The device comprises a sensor including at least one sensor element and a sample collection unit configured to collect a sample. The sample is applied to the sensor for detection of the presence of at least one chemical or biological entity.

In another aspect, a device is provided. The device comprises a sensor including at least one sensing element and an integrated circuit. The integrated circuit is configured to electrically drive the sensor and to process at least one electrical signal received from the sensor. The signal represents the presence or absence of a selective chemical or biological entity.

Other aspects will be understood from the following description.

DETAILED DESCRIPTION

A semiconductor sensor-based near-patient diagnostic system and related methods are described herein.

Sensor Architecture

The semiconductor industry has long demonstrated how miniaturization can result in cost reduction without sacrificing capability. This application is focused on incorporating semiconductor-processing techniques to develop nanoscale processor chips and systems for simultaneous diagnosis and/or prognosis of multiple disease biomarkers, tumor cells and other relevant analytes.

Figure 1:
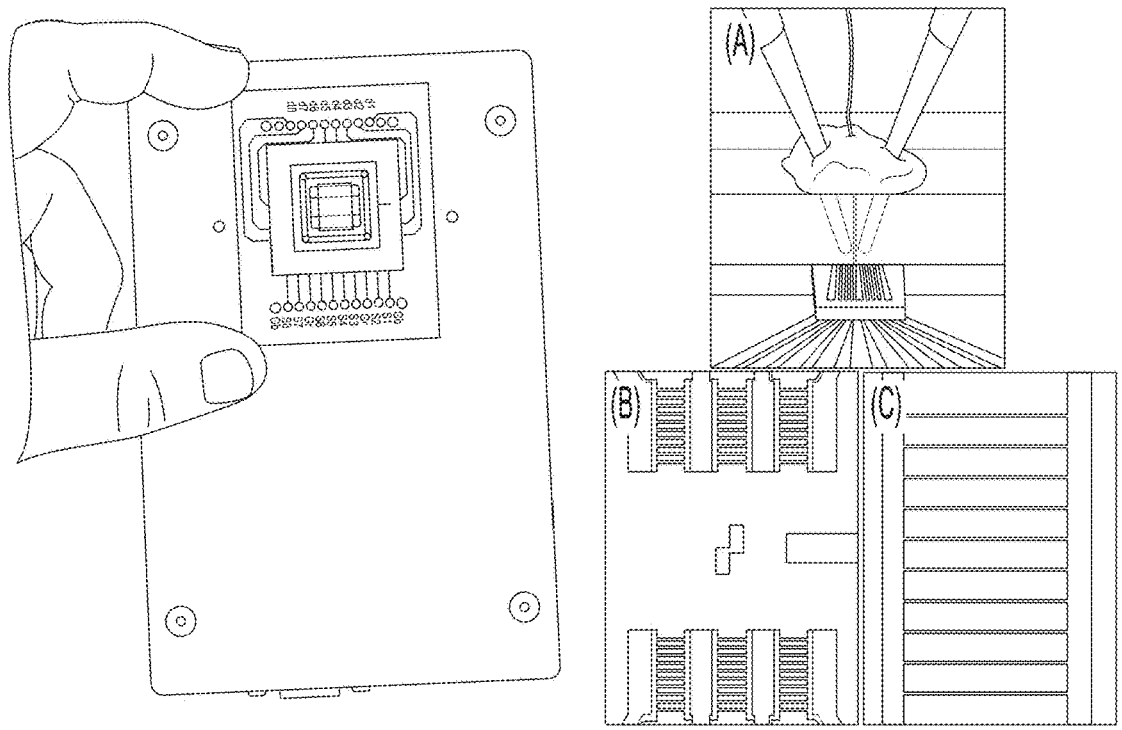
FIG. 1 shows (Left) Photograph of prototype device (black box) with an exposed multiplexed sensor, with fluidic chamber mated to silicon sensor element; and (Right) Optical micrograph of device showing fluidic connections and electrodes, including electron micrograph of sensor array.

FIG. 1 shows a prototype (black box) with the exposed multiplexed sensors, functionalized and capable of detecting multiple biomarkers at the same time. The presence of a biomarker is detected by a nanoscale field-effect transistor sensor through the measurement of conductance change of bio-functionalized nanowires. These nanoscale sensors serve as fundamental building blocks of our proposed sensor chip. The change in conductance is primarily due to the contribution of surface (charge) states to the conductance, which for larger sensors is dominated by volume effects. The fractional change is greatest for the smallest sensors, due to the increased surface-to-volume ratio. The presence of charged proteins on the surface of an active nanowire induces a large fractional change in the nanowire conductance, and enables relatively easy detection.

Nanoscale ion-sensitive FET (field effect transistor), fabricated with a "bottom-up" method, has been shown to be an effective way to monitor the concentration of homogeneous chemical and biological entities in the solution by detecting the changes in the surface potential, due to either point charges or dipoles associated with biomolecules. In contrast, we adopt a "top-down" method for device fabrication and create a nanoscale biosensor with complete control of the geometry, allowing for operation under conditions of controlled bias. The geometry and alignment of the nanowire can be fully controlled by lithography and standard semiconductor processing techniques in a CMOS-compatible process. The silicon nanowires are fabricated from Silicon-On-Insulator (SOI) wafer by electron beam lithography and surface nanomachining, which provide highly controllable nanowire sensors in comparison to other nanoelectronic approaches.

With recent advances in nanotechnology, it is now possible to combine high sensitivity at a resolution of sub-ng/ml, with multiplexing. We propose to investigate the feasibility of incorporating multiple sensors on a single chip module, laying the foundation for later studies that may lead to a high-throughput, sensitive, parallel biosensor chip for cancer markers based on nanotechnology methods.

Since the critical dimensions of the nanowires range between 50-100 nm, these devices can also be manufactured using optical lithography in standard semiconductor foundries.

Figure 2:
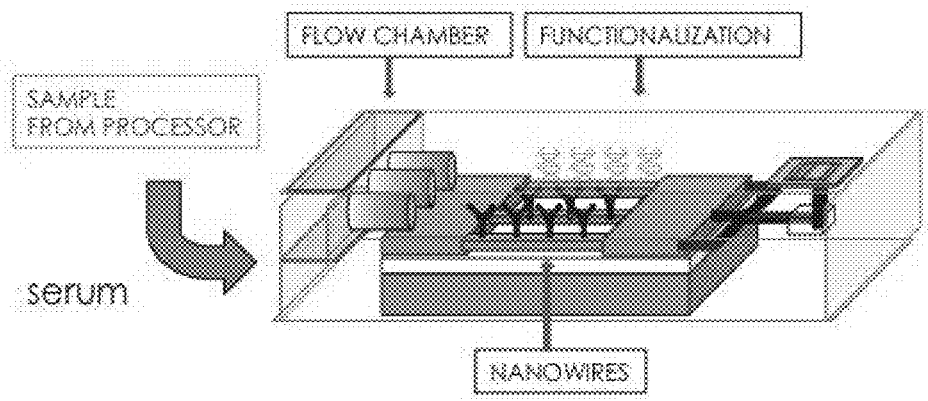
FIG. 2 shows A system flow diagram of the nanowire sensor and the microfluidic system.

FIG. 2 shows a system flow diagram. Fluid sample is injected into a fluid chamber that contains the nanosensors. PDMS gel is used to seal the device and surround the nanowire, which is bathed in a fluid volume of 30 microL, connected to a syringe pump. The size of the cell represents a compromise between diffusion and advection, and the limitation set by the pressure gradient required to drive the solution past the nanochannel surface. The measurement circuit includes a small AC (alternating current) modulation, superimposed on the DC (direct current) bias across the nanowire. The AC-modulation voltage and the DC bias voltage are added by a non-inverting summing circuit integrated with the preamplifier circuit. Differential conductance measurements are taken by sweeping the DC bias at constant AC modulation amplitude. The quantity of interest is delta G, the change in the differential conductance due either to a change in the reference gate voltage delta $V_g$, or to a change in molecular concentration delta m.

A potential applied to the top gate $V_t$ sets up an electric field that modulates the conductance channel between source and drain, and can be used to amplify small signals. If the top gate is replaced with functionalized surface binding sites, the binding of charged molecules will change the surface potential in addition to reference gate voltage $V_{rg}$. This surface potential change can modulate the conductance between source and drain. There is an equivalence between the conductance modulation produced by a change in the analyte concentration, and that produced by a change in the top gate voltage.

Small changes in the conductance of the device can be measured by considering the differential conductance with the derivative taken at constant $V_t$. This method yields measurements at higher signal-to-noise ratio compared to digital method of taking derivatives. The differential conductance G depends on top gate voltage $V_t$ or analyte concentration m in solution as well as bias voltage $V_{ds}$. As mentioned above, measurement is needed of the change in conductance delta G, due either to a change in the top gate voltage $V_t$, or due to change in concentration delta m. Higher signal delta G can be obtained in the region of negative $V_{ds}$ or positive $V_t$ for our nanosensor.

Device Architecture

The basic structure of the device contains the following elements:
1) A sensor module comprising of the sensor chip, capable of sensing analytes (markers and/or biological entities);
2) A reader module capable of sending control and command to the reader to perform the necessary task, sending additional information such as calibration data for on-chip data processing, reading out the sensor data and sharing data;
3) A communication channel, either wired or wireless, so that the reader and the sensor can have a two-way communication.

Figure 3:
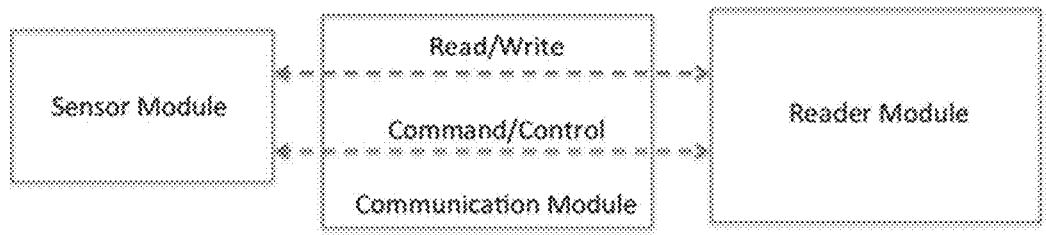
FIG. 3 shows the basic system architecture containing a sensor module, a reader module and a method to communicate.
Figure 4:
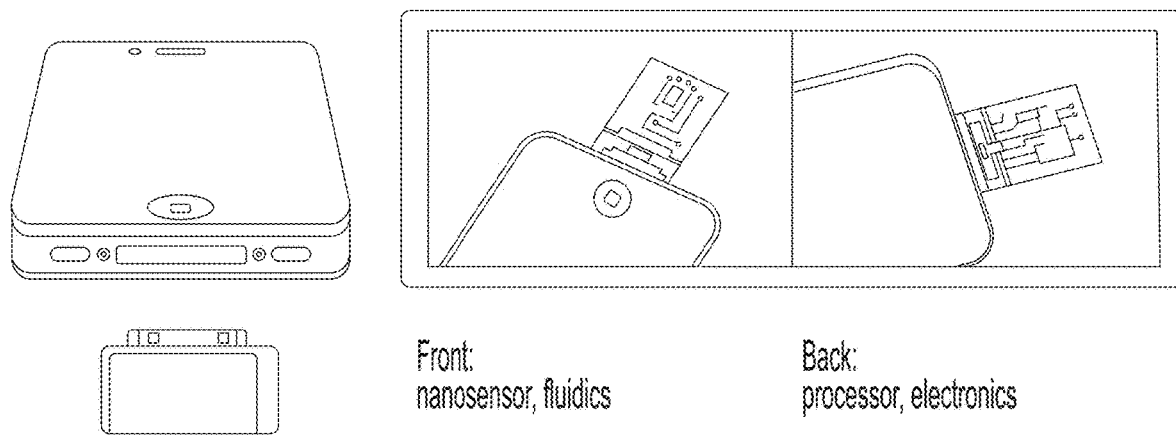
FIG. 4 shows (Left) Device configuration involving a disposable plugin cartridge to be used with a smartphone; and (Right) A prototype (designed for biomarker detection with discrete electronics). The front part of the PCB (printed circuit board) contains the sensor and microfluidics, and the back part contains the measurement and processing circuit.

In addition to the basic configuration, shown in FIG. 3, the reader module may also contain necessary electronics to share or receive data and command/control sequence with another system capable of performing analytics. This system could be a cloud computer or a network that may communicate with the reader through either wired or wireless communication. The analytics performed by this system may provide an actionable decision or support data and analysis for a clinician or healthcare professional to make that decision.

Depending on application, the device configuration will build on this elementary system architecture. In order to elucidate this application-specific device configuration, it is important to understand the range of device applications, as listed in Table 1 below.

Implantable Device

In one embodiment, the device could be implantable, where the device is embedded inside the body for diagnosis or monitoring. For instance, it could be a continuous glucose monitoring device that detects glucose in blood, tear or interstitial fluid. What is implanted is the sensor module depicted in FIG. 3. The reader module could be a handheld or table-top device capable of communicating with the implanted module, typically wirelessly. In addition, the reader module may be used for wireless charging of the implanted sensor module for long-term operation. The reader module could be a modified smartphone or bracelet that can be worn by the patient. Furthermore, an implanted module could also contain a drug delivery system for remote release of the appropriate drug into the body. For instance, an implantable glucose monitoring device could contain an insulin delivery module that can release insulin into the bloodstream depending on the blood sugar level. In a different configuration, a glucose sensor can be implanted in the eye for detecting glucose level in the tear.

TABLE 1

Device Categories

Implantable device
Subcutaneous device
E-patch
E-tattoo
Wearable (ring, bracelet, watch)
Smartphone plugin
Handheld device
Tabletop box
Central lab equipment Subcutaneous Device In another configuration as a subcutaneous device, the sensor module can be located on the skin or under the skin. In certain applications, the device can be embedded under the skin or applied as a patch. The sensor module can access a range of analytes in this configuration. These analytes can be detected in blood vessels and nerves in the dermis. There are also different types of cells found in the hypodermis, which include adipose cells, fibroblasts and macrophages. In addition to these cells, the body also secretes an oily, waxy matter called sebum through what are known as the sebaceous glands. The sebum mostly contains triglyceride, squalene, wax esters and metabolites of usually fat producing cells. In addition, secretion rate of sebum can be used to monitor some hormones such as testosterone, estrogen, and progesterone. The sensor module can be configured to detect these elements in the sebum, which can be used as markers for diagnosis or monitoring of specific diseases. Sensing of analytes in the sebum can also be used for diagnosis of infectious diseases (bacterial or viral infection) and inflammation. Similar to the glucose-insulin integrated system discussed above, a subcutaneous device can be used to both detect analytes and deliver drugs that may include hormones, antioxidants, anti-inflammatory and antimicrobial lipids. Other variations of a subcutaneous device could be an electronic patch (e-patch) or an electronic tattoo (e-tattoo), located on the skin or under the skin.

Wearable Device

In yet another configuration, the sensor module and the reader module can be combined as a single wearable device. Examples of this include arm and leg bracelets, earrings and other wearable configurations on the body. In one variation, the device can be worn as a wrist watch, which contains the sensor and the reader with connectivity. Fluid sample from the body such as a drop of blood can be applied to an exposed surface of the device, which will sense the desired analyte in the fluid sample. In another variation, it is possible to connect a disposable cartridge, which can be plugged into the device. The cartridge will contain the appropriate fluid sample to be tested.

Smartphone Plugin

In another configuration, the sensor module can be a plugin cartridge for a smartphone or a smartphone configured as a reader with essential functionalities such as connectivity and basic data processing capabilities with an app. The plugin cartridge can be connected directly into a smartphone or smartphone-like reader, or the cartridge can be linked with the reader by near field communication (NFC) such as Bluetooth. Typically, the user interface or an app can be used to enable measurement and presentation of the marker levels in the fluid sample. In addition, connectivity (cellular, WiFi, Bluetooth, GPS etc) is used to share, store and/or analyze data with a system at a remote location.

Handheld Device

In the handheld device configuration, the reader module is similar to the smartphone-like reader described above. It can use either a disposable plugin cartridge or it can be an integrated system containing the sensor module inside, so a fluid or other samples can be presented to the device for testing. Because of the superior multiplexing capabilities of the semiconductor sensors, it is possible to detect multiple test panels simultaneously.

Table-Top Device and Central Lab Equipment

In this standard configuration, it is possible to considerably increase the system functionality by having test menus that can be adapted to any application. Most disease types can be covered by a panel of 100-150 analytes with a single test, and test types can include protein markers, genetic markers, circulating cells and other entities such as bacteria and virus. In addition to testing for certain diseases, such all-inclusive tests can also be used for wellness checks, where a comprehensive (male or female) wellness panel can further include standard panels such as complete blood count (CBC) or metabolic panel.

System-Level Architecture

Figure 5:
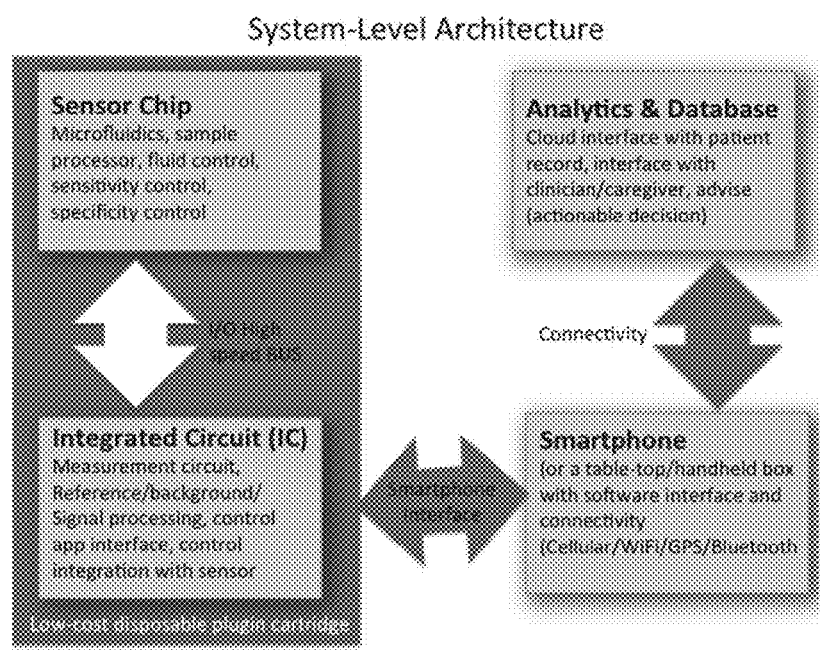
FIG. 5 shows a system-level architecture of the proposed multiplexed biomarker assay system. The (disposable) plugin cartridge will contain the nanosensor chip and the integrated circuit. A smartphone or a handheld box with smartphone functionalities will interface with the disposable plugin cartridge for data acquisition, analysis and management.

The complete system comprises of the two modules, sensor module and reader module, discussed above. In addition, it includes remote or on-board analytics for data analysis, processing and bioinformatics, necessary to arrive at actionable decision for the care provider. FIG. 5 elucidates an example where a smartphone plus plugin cartridge system connects wirelessly to a remote analytics/database system for further data processing. For example, a test panel including a number of biomarkers may require multivariate regression analysis to provide the necessary analytics for actionable decision. The analysis may include patient's personalized data to create a profile for each test to aid the clinician with their decision making process.

Table 2 lists examples of two panels, one for heart attack and the other for stroke. These panels include multiple tests that must be performed quickly in certain situations for actionable decision towards patient care. In addition to such time-sensitive tests, there are tests, results of which might necessitate further tests.

TABLE 2

Cardiac panel

| | |
|---|---|
| Cardiac-Heart Attack | Troponin, BNP, Glucose, Electrolytes, BUN/Creatnine, CBC, Lipids |
| Cardiac-Heart Failure | BNP, pro-BNP, BUN/Creatnine, K+, Na+, Glucose, Hgb/Hct, WBC, Platelets |

Treatment Pathway—Test Panel Algorithm

Figure 6:
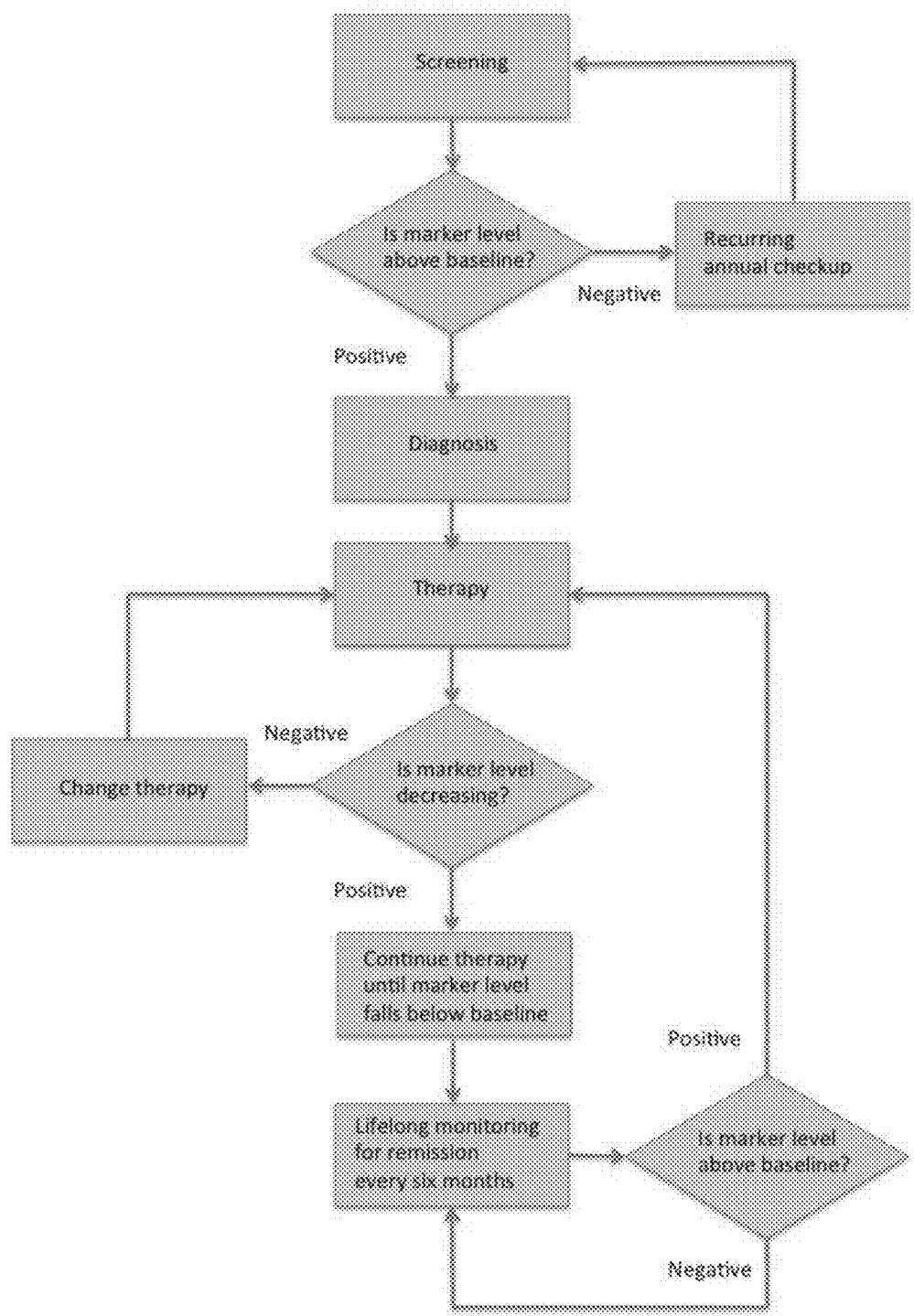
FIG. 6 shows a treatment pathway involving a single marker

Most markers can be used for screening, diagnosis, staging, prognosis or monitoring for therapy responsiveness, and monitoring for remission. Different stages in this care continuum usually correspond to different levels (or concentrations) of the biomarker(s). FIG. 6 shows a treatment pathway involving a single marker. Similar pathways can be developed for test panels that contain tests of multiple markers. Certain marker levels may need to be monitored much more frequently, which necessitates for those tests to be done at the patient's home, without requiring the patient to make frequent hospital visits. The system architecture described earlier enables home testing, where the data can be remotely shared with the clinicians and care providers, almost instantly.

The invention claimed is:

1. A computerized method comprising:
receiving analyte data from a reader device via a communication channel with the one or more reader device, wherein:
the analyte data is based on sensor data received from a sensor device in communication with the reader device;
the sensor data is indicative of whether an analyte was present in a fluid sample tested using a set of sensor elements of the sensor device;
the sensor data is based on at least one electrical signal received from the sensor device determined by electrically driving a set of sensor elements while in fluid communication with the fluid sample;
electrically driving the set of sensor elements comprises applying an alternating current modulated on a direct current bias across at least one nanowire of the sensor element of the set of sensor elements;
storing the analyte data in a database; and
processing at least a portion of the analyte data in the database system to generate data.

2. The computerized method of claim 1, wherein processing the portion of the analyte data in the database system comprises performing a test panel of a plurality of analytes for a patient associated with the portion of the analyte data.

3. The computerized method of claim 1, wherein receiving the analyte data from the reader device via the communication channel with the reader device comprises receiving at least a portion of the analyte data via a wireless communication channel.

4. The computerized method of claim 1, wherein receiving the analyte data from the plurality of reader device via the communication channel with the reader device comprises receiving at least a portion of the analyte data via a wired communication channel.

5. The computerized method of claim 1, wherein the sensor element comprises a source and a drain, and the at least one nanowire of the sensor element is in electrical communication with the source and the drain.

6. The computerized method of claim 1, wherein the at least one nanowire of the sensor element comprises a set of surface binding sites configured to bind to one or more charged molecules in the fluid sample, such that the sensor element is configured to operate as a field effect transistor.

7. The computerized method of claim 1, wherein the set of sensor elements comprises a plurality of silicon sensors, and wherein electrically driving the set of sensor elements comprises electrically driving the plurality of silicon sensors.

* * * * *